(12) United States Patent  (10) Patent No.: US 7,419,262 B2
Whalen  (45) Date of Patent: Sep. 2, 2008

(54) DIRECT VIEW GONIO LENS

(75) Inventor: Paul C Whalen, Maple Valley, WA (US)

(73) Assignee: Ocular Instruments, Inc., Bellevue, WA (US)

( * ) Notice: Subject to any disclaimer, the term of this patent is extended or adjusted under 35 U.S.C. 154(b) by 0 days.

(21) Appl. No.: 11/506,670

(22) Filed: Aug. 18, 2006

(65) Prior Publication Data

US 2008/0043199 A1  Feb. 21, 2008

(51) Int. Cl.
*G02C 7/02* (2006.01)
(52) U.S. Cl. .................. 351/174; 351/219; 351/160 R
(58) Field of Classification Search ............. 351/174, 351/219
See application file for complete search history.

(56) References Cited

U.S. PATENT DOCUMENTS

| | | | |
|---|---|---|---|
| 3,820,879 A | 6/1974 | Frisen | |
| 3,943,931 A | 3/1976 | Krasnov | |
| 4,033,679 A | 7/1977 | Sussman | |
| 4,439,026 A | 3/1984 | Wilms | |
| 4,664,490 A | 5/1987 | Rol | |
| 4,907,872 A | 3/1990 | Schirmer | |
| 5,200,773 A * | 4/1993 | Volk | 351/219 |
| 5,252,998 A | 10/1993 | Reis et al. | |
| 5,501,217 A | 3/1996 | Ishiguro et al. | |
| 6,698,886 B2 * | 3/2004 | Pollack et al. | 351/219 |
| 6,976,758 B2 | 12/2005 | Khaw et al. | |
| 7,125,119 B2 * | 10/2006 | Farberov | 351/219 |
| 2006/0050229 A1 | 3/2006 | Farberov | |

FOREIGN PATENT DOCUMENTS

| | | |
|---|---|---|
| EP | 1464271 A1 | 10/2004 |
| GB | 782295 | 9/1957 |
| WO | 90/15570 A1 | 12/1990 |
| WO | 97/13453 A1 | 4/1997 |
| WO | 01/95842 A1 | 12/2001 |

OTHER PUBLICATIONS

Direct View Gonio Lens, *Ocular Instruments, Inc. Catalog*, 1987, 2 pages.
Iwasaki, N., et al., "The Double-Mirror Gonioscopic Lens for Surgery of the Anterior Chamber Angle," *Arch. Ophthalmol.* 115:1333-1335, Oct. 1997.
*Osher Surgical Viewing Kit*, 1-page product brochure.

* cited by examiner

*Primary Examiner*—Jessica T Stultz
(74) *Attorney, Agent, or Firm*—Christensen O'Connor Johnson Kindness PLLC

(57) ABSTRACT

A lens for viewing the anterior chamber of the eye includes a contact lens having a contact lens surface and an anterior surface. The anterior surface has an optical axis that intersects the optical axis of the contact lens surface. First and second mirror surfaces are positioned to redirect light rays from the periphery of the anterior chamber and reflect them in a direction parallel or nearly parallel to the optical axis of the contact lens surface.

10 Claims, 5 Drawing Sheets

DIRECT VIEW GONIO LENS

FIELD OF THE INVENTION

The present invention relates to lenses utilized in the examination and treatment of the eye and, more particularly, to lenses utilized in viewing the periphery of the anterior chamber of the eye.

BACKGROUND

A common lens utilized in connection with gonioscopy, i.e., the viewing of the periphery of the anterior chamber of the eye, is known as the Swan-Jacob Gonioprism (the "Swan") lens. The Swan lens comprises a contact lens having a posterior contact surface that conforms to the anterior surface of the cornea of an eye. The contact surface is generally spherical and has an optical axis that may be aligned with the optical axis of the eye. The contact lens also has an anterior surface that is offset in an anterior direction from the contact surface. More particularly, the anterior surface has an optical axis that intersects the optical axis of the contact surface. When the contact lens is positioned on the eye, the user may view the anterior chamber by looking into the anterior surface in a direction generally parallel to the optical axis of the anterior surface of the lens. The contact surface may be smaller than the cornea so that the lens can be moved around on the cornea to view various parts of the anterior chamber.

It is desirable to be able to view the periphery of the anterior chamber when the user's line of sight is along the optical axis of the eye. This is difficult or impossible to do with a Swan lens.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A preferred embodiment of the present invention, therefore, provides a lens system for viewing the anterior chamber of the eye in a direction along or near the optical axis of the eye utilizing the Swan-type lens. The lens comprises a contact lens element having a posterior concave contact lens surface compatible with the cornea of the eye. The contact lens surface has a contact optical axis. The contact lens has a curved anterior surface spaced from the contact lens surface. The anterior surface has an optical axis that may intersect, be offset from, or be coincident with the contact optical axis.

A first mirror surface is offset from the anterior surface of the contact lens element in an outward direction from the contact optical axis. A second mirror surface is offset from the contact optical axis, preferably in a direction opposite from said first mirror surface and angled away from the contact optical axis as the second mirror surface extends in an anterior direction. Preferably, the first mirror surface is offset from the anterior surface sufficiently to provide a visual gap between the contact lens and the first mirror surface along a sightline parallel to the contact optical axis.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
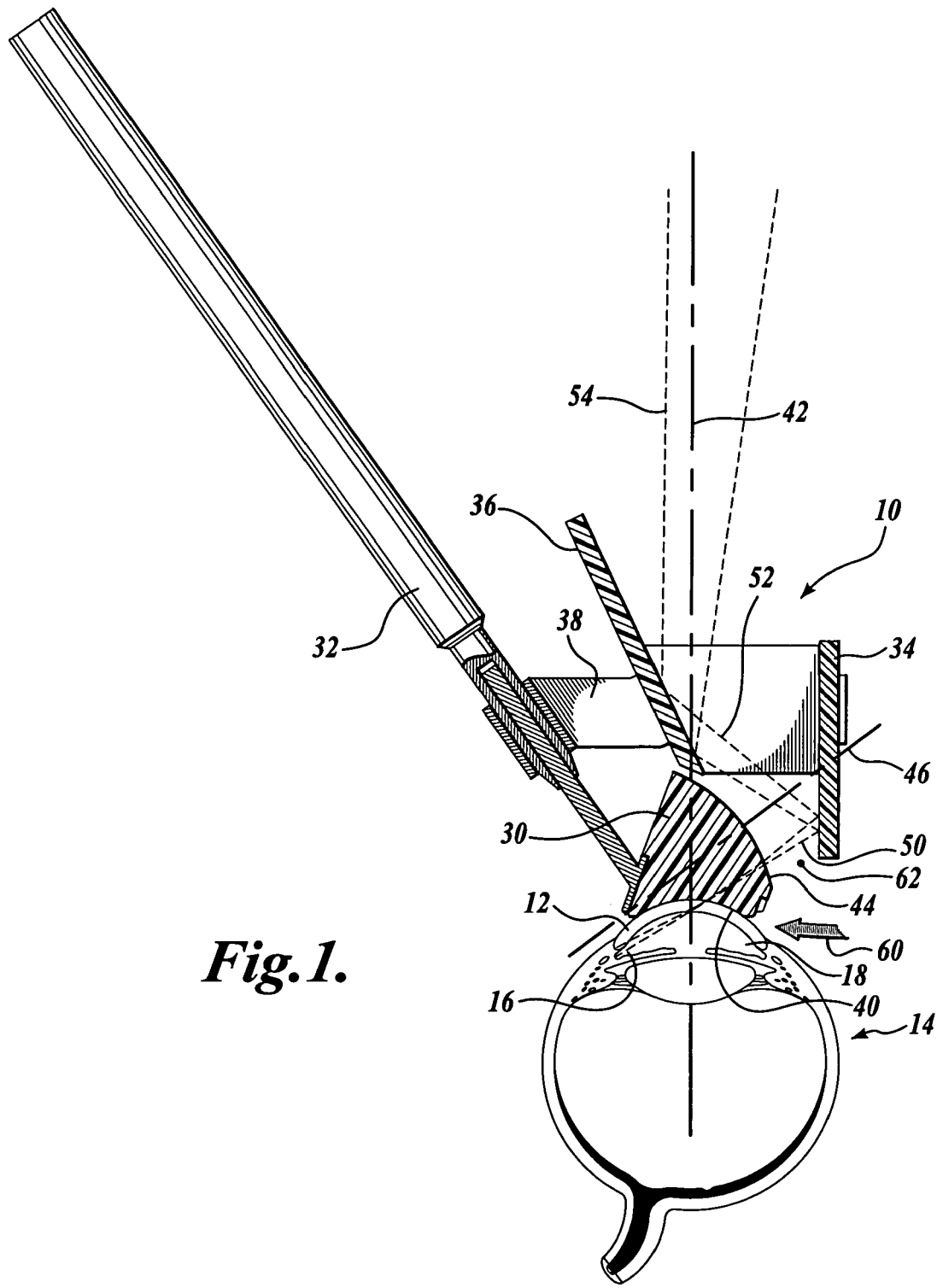
FIG. 1 is a view of the lens system of the present invention shown in conjunction with a human eye.
Figure 2:
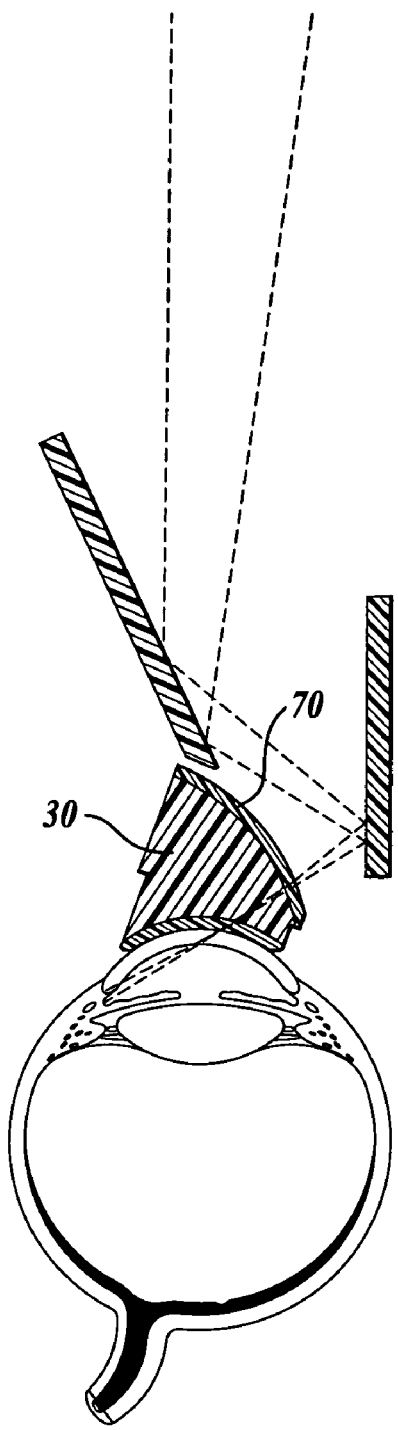
FIG. 2 is an alternate embodiment of the system of FIG. 1 showing a compound contact lens.

Referring now to FIG. 1, the lens system 10 of the present invention is shown in contact with the cornea 12 of an eye 14. The lens is designed to view the periphery 16 of the anterior chamber 18 of the eye. In a preferred embodiment, the lens comprises four elements, a contact lens 30, a holder 32, and first and second mirror elements 34 and 36. Mirror elements 34 and 36 are held by a bracket 38 that is attached to the proximal end of the holder 32 adjacent the contact lens 30. Referring now to FIGS. 1 and 2, the contact lens 30 has a posterior surface 40 that is concave in shape and conforms to and is compatible with the cornea of an eye. Typically, the posterior or contact lens surface 40 is spherical for ease of manufacture. The contact lens surface 40 has an optical axis 42 that is utilized here for purposes of reference. The contact lens also has an anterior surface 44 that is positioned anterior to the contact lens surface 40. The anterior surface 44 may be spherical or aspherical and has an optical axis 46. The optical axis 46 of the anterior surface 44 preferably intersects the optical axis 42 of the contact lens surface 40. In the embodiment as shown, a majority of the anterior surface 44 is offset to a first side (right side in the FIGURE) of the optical axis 42. To view the periphery of the anterior chamber of the eye utilizing only the contact lens surface, the viewer must view in a direction along or substantially parallel to the optical axis 46 of the anterior surface 44 of the contact lens.

In accordance with the present invention, a pair of mirrors 34 and 36 are mounted in an orientation relative to the contact lens so as to redirect light rays emanating from the anterior surface of the contact lens in a direction that is parallel or nearly parallel to the optical axis of the contact surface of the contact lens 30. The first mirror 34 has an inwardly facing mirror surface that is offset in a first direction from the optical axis 42 of the contact lens surface. Preferably, the mirror 34 is offset sufficiently from the contact lens so as to leave a visual gap between the mirror 34 and the posterior portion of the contact lens 30 so that the eye and, particularly, the peripheral portion of the cornea can be seen by the user looking in a direction parallel to or nearly parallel to the optical axis of the contact surface 40. The second mirror set is offset in an opposite direction from the first direction (to the left in the FIGURE) of the optical axis 42 of the contact lens surface. It is angled in a posterior-to-anterior direction away from the optical axis 42 of the contact lens. Mirrors 34 and 36 thus take the light rays 50 emanating from the contact lens 30 and reflect them along a path 52 in an upwardly and anterior direction where they are reflected by the mirror 36 in a direction 54 nearly parallel to or parallel to the optical axis 42 of the contact lens surface.

This arrangement allows the user to view the periphery of the anterior chamber when the contact lens is generally centered on the eye so that the optical axis 42 of the contact lens surface is oriented parallel to or nearly parallel to the optical axis of the eye 14. This eases use of the contact lens. Furthermore, when conducting surgery using the lens of the present invention, a scalpel used to enter the anterior chamber in the direction of arrow 60 can be viewed through the gap 62 as it is positioned to better view the peripheral portion of the cornea so as to conduct a goniotomy on the opposite side of the anterior chamber as shown in FIG. 1.

The lens system of FIG. 2 differs from that of FIG. 1 only in that a compound lens element 70 is employed on the contact lens 30. Otherwise, the construction and operation is the same.

Figure 3:
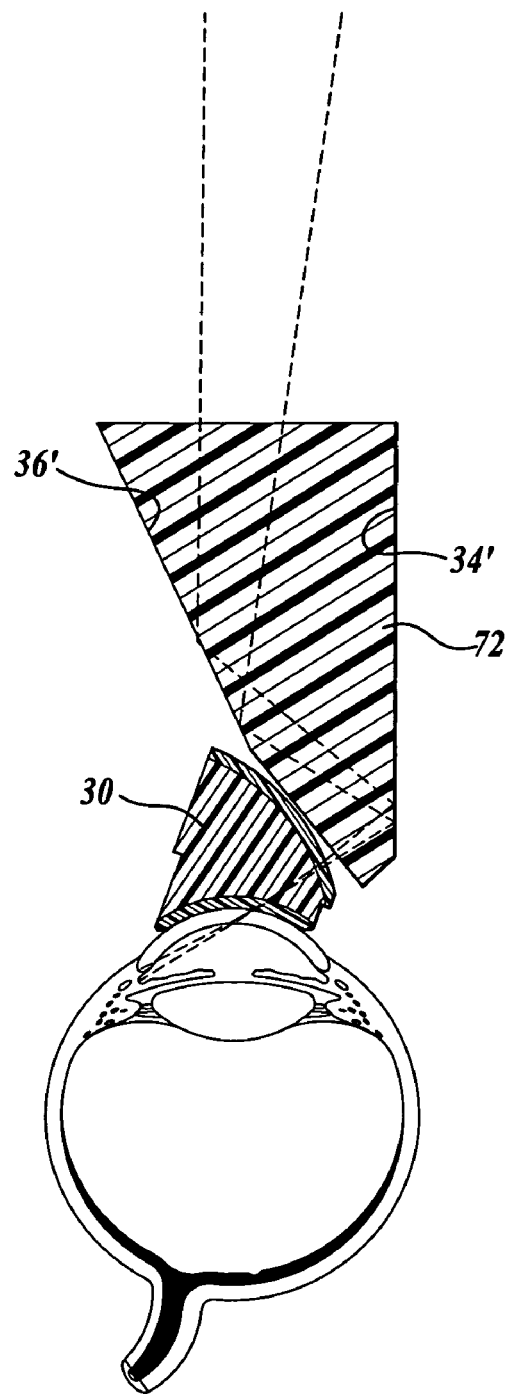
FIG. 3 is an alternate embodiment of the invention showing a compound contact lens and a prism mirror system.

As shown in FIG. 3, a prism 72 is substituted for the mirrors 34 and 36. The internal surfaces 34' and 36' function in a manner identical to the mirrors 34 and 36 shown in FIG. 1. In this embodiment, again, the contact lens element has a compound element set.

Figure 4:
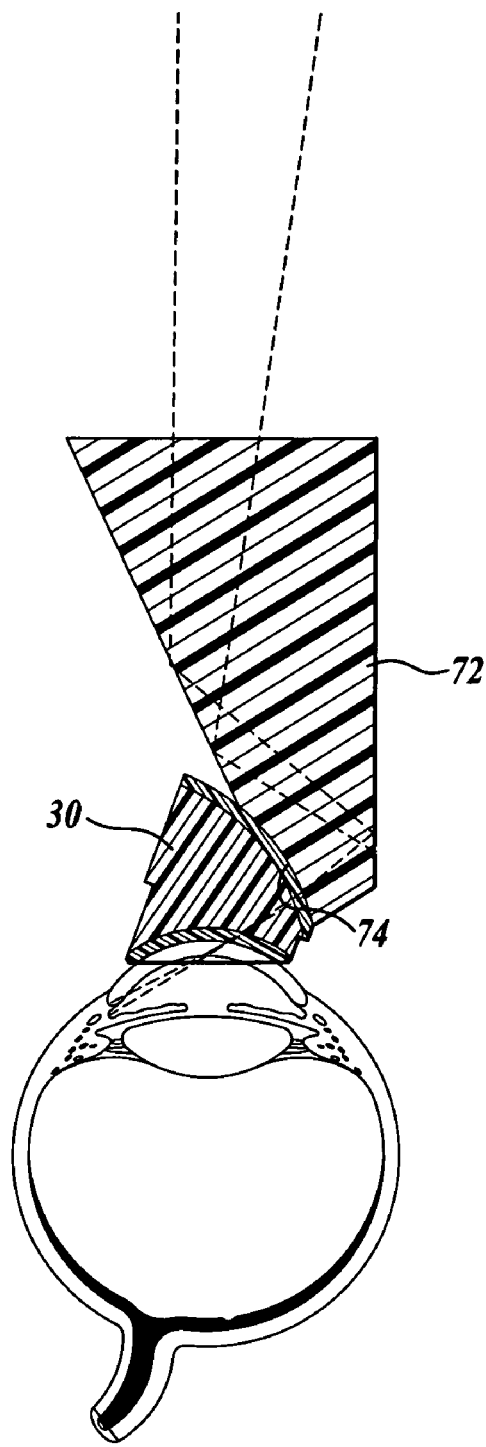
FIG. 4 is an alternate embodiment of the invention similar to FIG. 3 showing the prism system of FIG. 3 mated with the anterior surface of the contact lens.

The lens system shown in FIG. 4 is very similar to that of FIG. 3, except that a posterior and interior portion of the prism 72 has a concave circular surface 74 that conforms to the anterior curved surface of the contact lens 30. The surfaces are optically coupled to reduce internal reflections.

Figure 5:
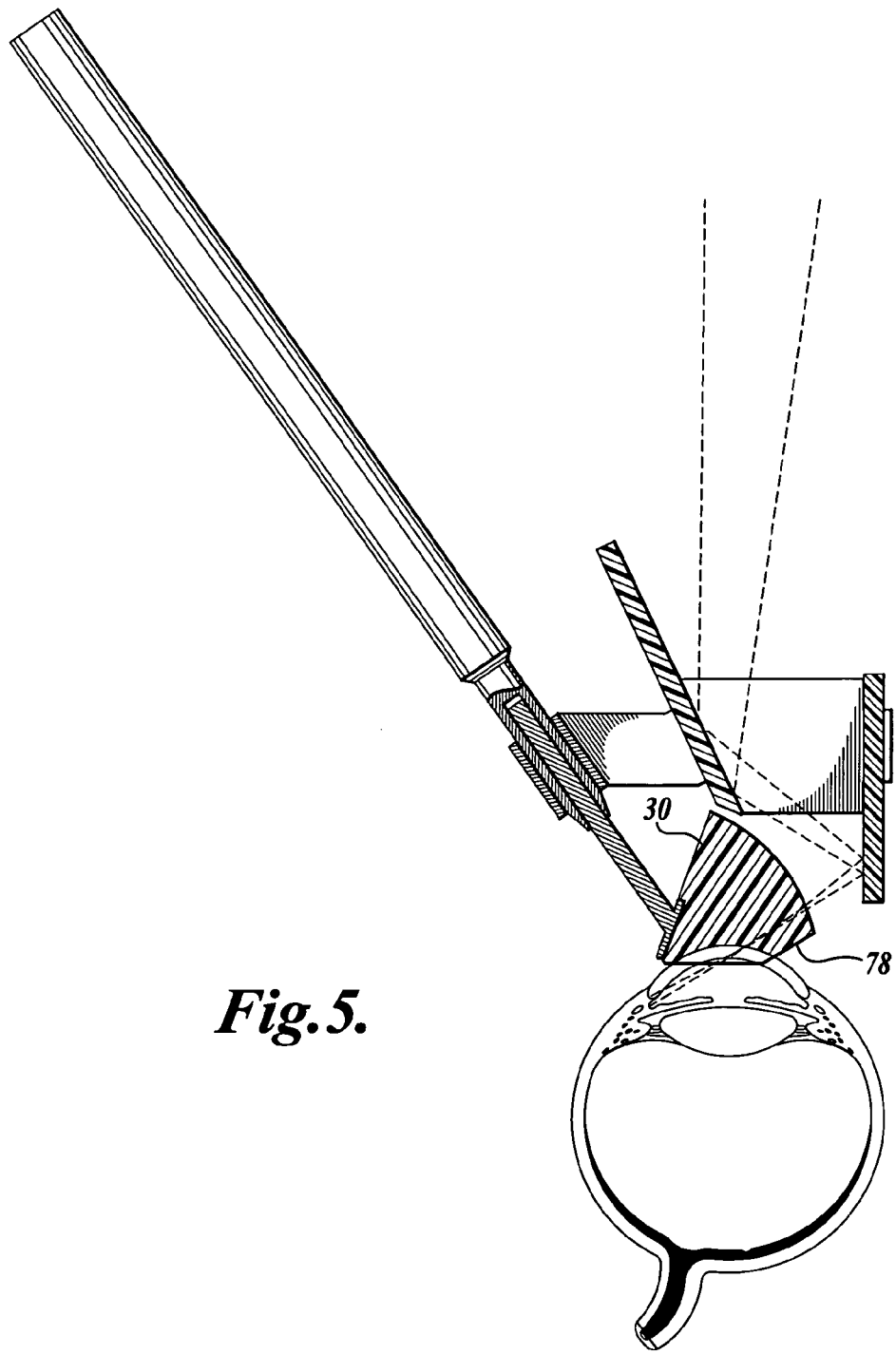
FIG. 5 is an alternate embodiment of the system of FIG. 1 showing a recess in a portion of the posterior section of the contact lens to allow freer access to the periphery of the cornea of an eye.

Finally, FIG. 5 is a variation of the embodiment shown in FIG. 1. The lower peripheral portion 78 of the contact lens 30 has been removed to form a recess that allows access to a larger portion of the periphery of the cornea. This embodiment would assist the user in inserting the scalpel to perform a goniectomy.

While illustrative embodiments have been illustrated and described, it will be appreciated that various changes can be made therein without departing from the spirit and scope of the invention.

The invention claimed is:

1. A lens for viewing the anterior chamber of an eye comprising:
    a contact lens element having a posterior concave contact lens surface compatible with the cornea of an eye, the contact lens surface having a contact optical axis, said contact lens having a curved anterior surface spaced from the contact lens surface, said anterior surface having an optical axis oriented at an angle to the contact optical axis;
    a first mirror surface offset from said anterior surface in an outward direction from said contact optical axis, a second mirror surface offset from said first mirror surface and angled away from said first mirror surface as said second mirror surface extends in an anterior direction, said first and second mirrors being arranged such that light rays emanating from the periphery of the eye pass through the contact lens and out of the curved exterior surface thereof and are first reflected from said first mirror surface toward said second mirror surface and then are reflected by said second mirror surface in a direction parallel or nearly parallel to said contact optical axis.

2. The lens of claim 1 wherein the optical axis of the anterior surface intersects the contact optical axis, and wherein said second mirror surface is offset from said contact optical axis in a direction opposite from said first mirror surface.

3. The lens of claim 2 wherein the posterior portion of said second mirror surface intersects said contact optical axis.

4. The lens of claim 3 wherein said first mirror surface is substantially parallel to said contact optical axis.

5. The lens of claim 4 wherein a portion of said second mirror surface is positioned anteriorly to said first mirror surface.

6. The lens of claim 5 wherein said first mirror surface is offset from said anterior surface to provide a visual gap therebetween along a sightline parallel to said contact optical axis.

7. The lens of claim 1 wherein said contact lens is a compound lens.

8. The lens of claim 1 wherein said mirror surfaces are mirrors.

9. The lens of claim 1 wherein said mirror surfaces are internal facets of a prism.

10. The lens of claim 1 wherein said contact lens is recessed in an anterior direction to provide access to the periphery of the cornea of an eye.

* * * * *